United States Patent [19]

Rebling et al.

[11] 4,239,761

[45] Dec. 16, 1980

[54] BASICALLY SUBSTITUTED UREAS AND PROCESSES FOR THE TREATMENT OF VIRUS DISEASES

[75] Inventors: Rolf Rebling; Gerhard Scheffler; Klaus Pressler, all of Bielefeld; Klaus D. Schenk, Steinhagen, all of Fed. Rep. of Germany

[73] Assignee: Asta-werke Aktiengesellschaft, Chemische Fabrik, Bielefeld, Fed. Rep. of Germany

[21] Appl. No.: 69,335

[22] Filed: Aug. 23, 1979

[30] Foreign Application Priority Data

Aug. 30, 1978 [DE] Fed. Rep. of Germany ....... 2837794

[51] Int. Cl.³ .................. C07D 295/10; C07D 295/16; C07D 295/22; A61K 31/495
[52] U.S. Cl. .................................... 424/250; 544/383; 544/390; 544/399
[58] Field of Search ...................... 544/383, 390, 399; 424/250

[56] References Cited

FOREIGN PATENT DOCUMENTS 2150438 10/1971 Fed. Rep. of Germany .

OTHER PUBLICATIONS

Wadia et al., Chem. Abstracts, vol. 52 (1958) 155, 47–48.

Primary Examiner—Henry R. Jiles
Assistant Examiner—R. W. Ramsuer
Attorney, Agent, or Firm—Schwartz, Jeffery, Schwaab, Mack, Blumenthal & Koch

[57] ABSTRACT

The present invention is related to new basically substituted ureas having the general Formula I

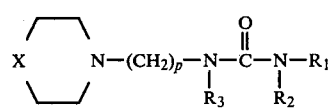

and the pharmaceutically acceptable acid addition salts thereof which produce an improved antiviral activity against DNS- and RNS-viruses. The invention is further related to the treatment of humans or animals suffering from diseases caused by viruses by administering compositions containing such ureas or salts thereof as active agent.

5 Claims, No Drawings

BASICALLY SUBSTITUTED UREAS AND PROCESSES FOR THE TREATMENT OF VIRUS DISEASES

The present invention is related to new basically substituted urea compounds and salts thereof which have a high antiviral activity against DNS- and RNS-viruses. The present invention is further related to processes for producing the same and to compositions comprising the same as active agent such compositions being useful in the treatment of diseases caused by viruses both in humans and animals.

The development of compounds having antiviral activity up to now yielded only into very few products which are actually used in the treatment of diseases caused by viruses. Furthermore, the known products used in antiviral chemotherapy or still in development to a great extent only show activity against a very limited spectrum of viruses covering only certain subtypes of viruses. On the other hand, the nucleoside analoga acting as antimetabolites show a considerable cytotoxic activity and severe influence upon the metabolism of healthy cells which activity may yield into severe undesirable side effects such as teratogenicity, anemia, ataxia, stomatitis, loss of finger nails, thrombocytopenia and the like. Other known compounds only act as unspecific immunstimulators.

The basically substituted ureas accordng to the present invention with improved antiviral activity correspond to the general Formula I

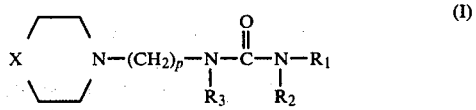

wherein
X is oxygen or the group $R_4$—N<,
p is 2 or 3,
$R_1$ is an alkyl group having from 6 to 18, preferably from 6 to 14 carbon atoms, most preferred in a straight chain,
$R_2$ and $R_3$, which may be the same or different, represent methyl or ethyl and
$R_4$ is methylsulfonyl, diethyl carbamoyl or the group

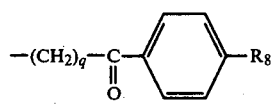

wherein q is 1 or 2, preferably 2, and $R_8$ is methyl, methoxy, chlorine, bromine, and preferably methyl, methoxy or chlorine. The invention embraces also the pharmaceutically acceptable salts thereof.

In view of their particularly high activity most preferred are (a) N,N'-dimethyl-N-tetradecyl-N'-[2-(1-diethyl carbamoyl-4-piperazinyl)-ethyl]-urea and the pharmaceutically acceptable salts thereof, in particular its hydrochloride (Formula I: X=>N—$R_4$, p=2, $R_1$=n—$C_{14}H_{29}$, $R_2$ and $R_3$=$CH_3$, $R_4$=diethyl carbamoyl);

(b) N,N'-dimethyl-N-tetradecyl-N'-{2-[1-(2-p-toluylethyl)-4-piperazinyl]-ethyl}-urea and the pharmaceutically acceptable salts thereof, in particular its dihydrochloride (Formula I: X=>N—$R_4$, p=2, $R_1$=n—$C_{14}H_{29}$, $R_2$ and $R_3$=$CH_3$, $R_4$=

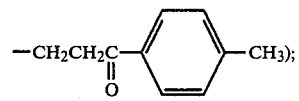

(c) N,N'-dimethyl-N-hexyl-N'-(2-morpholino-ethyl)-urea and the pharmaceutically acceptable salts thereof, in particular its hydrochloride (Formula I: X=O, p=2, $R_1$=n—$C_6H_{13}$, $R_2$ and $R_3$=$CH_3$).

The compounds according to the present invention and the pharmaceutically acceptable salts thereof are characterized by a broad spectrum of antiviral activity covering both DNS- and RNS-viruses. The compounds have a low toxicity and a direct activity to the replication cyclus of the viruses.

The compounds according to the present invention and the salts thereof are useful in human medicine, in particular for the topical treatment of diseases caused by viruses, in particular diseases of the skin, of the cornea of the eyes and of mucous membranes. Examples for such diseases are herpes labialis, herpes genitalis, herpes corneae (herpes ceratitis), herpes zoster, exzema vaccinatum, vaccina progressiva gangrenosa, stomatitis aphthosa or condylomata acuminata. Furthermore, the compounds are useful for the systematical prophylaxes or therepeutic treatment of acute viral infections of the upper respiratory tract such is influenca, bronchitis, rhinitis, rhinopharyngitis, as well as of acute viral infections of the central nervous system such as herpes encephalitis, and of virus hepatitis. Furthermore, the products are very useful in the treatment of many diseases of animals caused by viruses.

The compounds are applied for topical uses in a dose range from 0.005 to 0.3, preferably 0.01 to 0.1 percent by weight and for parenteral uses at a daily dose ranging from 5 to 250, preferably 10 to 200 mg per kg body weight depending upon the weight of the species to be treated, and for systemic oral uses in humans at a daily dose of about 300 mg.

The ureas according to the present invention and the pharmaceutically acceptable salts thereof may be produced by any of the processes given hereinafter and known as such:

(A) a compound of the general Formula II is subjected to reaction with a compound of the general Formula III

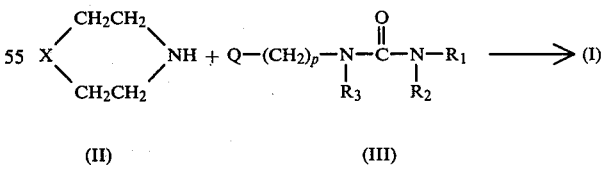

wherein X, p, $R_1$, $R_2$ and $R_3$ have the same meaning as given for Formula I and Q is a halogen atom or an alkyl sulfonyloxy group, in particular a lower alkyl sulfonyloxy group wherein the alkyl group has 1 to 6 carbon atoms;

(B) a compound of the general Formula IV is subjected to reaction with a compound of general Formula V

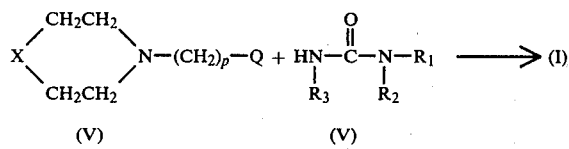

(V)     (V)

wherein X, p, R₁, R₂ and R₃ have the same meaning as given for Formula I and Q has the same meaning as given for Formula III;

(C) a compound of the general Formula VI is subjected to reaction with a compound of the general Formula VII

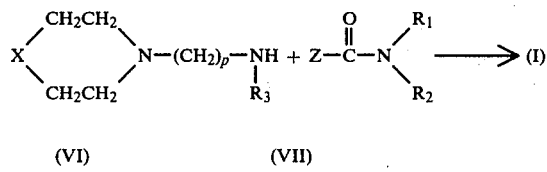

(VI)     (VII)

wherein X, p, R₁, R₂ and R₃ have the same meaning as given for Formula I and Z is a groupment such as a halogen atom, an alkoxy group, a phenoxy group or an imidazolyl group, or forms a double bond as

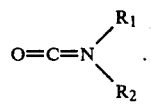

The compounds according to Formula I may be furthermore produced by subjecting a compound of Formula I, wherein R₂ and/or R₃ represent hydrogen, to reaction with a suitable alkylating agent such is an alkyl halogenide or an alkyl ester of a sulfuric acid or of a sulfonic acid which reaction is known as such.

All of the above methods for producing the compounds according to the present invention are carried out in suitable organic solvents. Preferably equimolar amounts of the reaction components are used. If Q and/or Z is a halogen atom, an acid binding agent may be used in an appropriate amount in order to neutralize the hydrohalogen acid H—Q or H—Z formed.

In the alkylating reaction B suitable solvents are benzene, toluene, dioxane and tetrahydrofurane and, above all, the dipolar aprotic solvents such as dimethylsulfoxide, dimethylformamide, acetonitril and the like. Suitable condensation agents (acid binding agents) are in particular alkali metal hydrides, amides, alcoholates or hydroxides. The reaction is carried out at temperatures between 0° C. and 110° C. depending upon the solvent and condensation agent actually used. The reaction A is carried out in a solvent as above enumerated or in a lower alcohol. Useful acid binding agents for this reaction are for instance potassium carbonate and in particular triethylamine. If no acid binding agent is used the corresponding salts of the claimed compounds are obtained directly. The addition of amines VI to isocyanates VII and the carbamoylation of amines VI (process C) is carried out in inert solvents, preferably in aromatic hydrocarbons such as benzene and toluene or in ethers such as dioxane and tetrahydrofurane. The reaction may be carried out in the presence of an acid binding agent such as triethylamine or pyridine. The reaction C is carried out at temperatures ranging from 0° C. and 110° C.

The starting products used in all of the processes above described are produced by standard methods. The carbamoyl compounds of general Formula VII, if not available as trade product, may be produced from the corresponding amines as described in Houben-Weyl Vol. 8, p. 119 to 128, or Vol. 8, p. 115 to 117. The ureas of the general Formula III and V are produced for instance as described in Houben-Weyl Vol. 8, p. 149 to 162.

The compounds of the general Formula I may be converted into acid addition salts. Useful acids for producing pharmaceutically acceptable acid addition salts are for instance hydrochloric acid, hydrobromic acid, sulfuric acid, phosphoric acid, methane sulfonic acid, acetic acid, lactic acid, fumaric acid, maleic acid, tataric acid, citric acid, salicic acid or embonic acid and the like.

The following examples serve to further illustrate the preparation of the compounds according to the present invention without however limiting the same thereto.

EXAMPLE 1

N,N'-Dimethyl-N-(n-tetradecyl)-N'-[2-(1-diethylcarbamoyl-4-piperazinyl)-ethyl]-urea

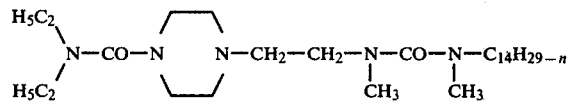

14.5 g (0.05 mole) of methyl-(n-tetradecyl)-carbamic acid chloride are dissolved in 20 cc. of toluene. This solution is added at room temperature with stirring dropwise to a solution of 12.1 g (0.05 mole) of 1-diethylcarbamoyl-4-(2-methylamino ethyl)-piperazine and 5.1 g (0.05 mole) of triethylamine in 40 cc. of toluene. After completion of the addition, the resulting mixture is stirred at about 100° for another hour. The precipitated triethylamine hydrochloride is filtered off from the cooled reaction mixture and the filtrate is evaporated. The residue is taken up in 150 cc. of ether, the ethereal solution is washed three times with 150 cc. of water each time and is dried over anhydrous Na₂SO₄. Upon evaporation of the ether, 23.5 g (94.8% of the theoretical) of the oily crude urea are obtained.

For preparing the hydrochloride, the crude urea is dissolved in anhydrous ether and the equivalent amount of an ethereal solution of HCl is added dropwise with stirring and cooling.

M.p.: 167° to 170° C. (recrystallized from acetic acid ethyl ester admixed with a small amount of methanol).

EXAMPLE 2

N,N,N'-Trimethyl-N'-[2-(1-diethylcarbamoyl-4-piperazinyl)-ethyl]-urea

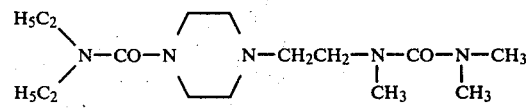

5.4 g (0.05 mole) of dimethyl carbamic acid chloride dissolved in 20 cc. of toluene are added dropwise with stirring at room temperature to a solution of 12.1 g (0.05 mole) of 1-diethylcarbamoyl-4-(2-methylamino ethyl)-piperazine and 5.1 g (0.05 mole) of triethylamine in 40 cc. of toluene. Thereafter, the reaction mixture is stirred for another hour at about 100° C. The reaction mixture is cooled and the precipitated triethylamine hydrochloride is filtered off with suction and the filtrate is evaporated. The residue is dissolved in 150 cc. of ether, the ethereal solution is washed twice with 150 cc. of 5 n NaOH each time and the resulting solution is dried over anhydrous Na2SO4. Upon evaporation of the ether, 15.3 g (97.6% of the theoretical) of the oily crude urea are obtained.

Hydrochloride: M.p.: 193° to 196° C. (recrystallized from aceton admixed with a small amount of methanol).

EXAMPLE 3

N,N'-Dimethyl-N-(n-decyl)-N'-[3-(1-diethylcarbamoyl-4-piperazinyl)-propyl]-urea

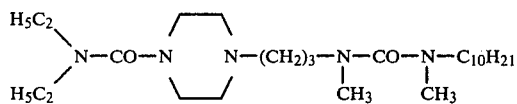

4.7 g (0.02 mole) of methyl-n-decylcarbamic acid chloride are added dropwise to 5.1 g (0.02 mole) of N-diethylcarbamoyl-N'-γ-methylamino-propyl-piperazine and 2 g (0.02 mole) of triethylamine in 50 cc. of dioxane. After completion of the addition, the resulting reaction mixture is stirred for another hour at room temperature, the precipitated triethylamine hydrochloride is filtered off with suction and the filtrate is evaporated in a vacuum.

For producing the hydrochloride, the obtained crude base is dissolved in anhydrous ether and an ethereal solution of HCl is added thereto. The hydrochloride is filtered off with suction and is further purified by recrystallization from acetic acid ethyl ester.

Yield: 4.3 g (43.9% of the theoretical).
M.p.: 112° to 114° C.

EXAMPLE 4

N,N'-Dimethyl-N-(n-tetradecyl)-N'-[2-(1-methanesulfonyl-4-piperazinyl)-ethyl]-urea

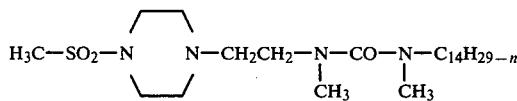

14.5 g (0.05 mole) of methyl-(n-tetradecyl)-carbamic acid chloride dissolved in 20 cc. of dioxane are added dropwise with stirring at room temperature to a solution of 11.1 g (0.05 mole) of 1-methanesulfonyl-4-(2-methylamino-ethyl)-piperazine and 5.1 g (0.05 mole) of triethylamine in 40 cc. of dioxane. The reaction mixture thereafter is stirred for one hour at about 100° C. After cooling, the precipitated triethylamine hydrochloride is filtered off with suction and the filtrate is evaporated. The residue is dissolved in 150 cc. of methylene chloride, the resulting solution is washed three times with 150 cc. of water each time and finally is dried over anhydrous Na2SO4. After removal the methylene chloride, the resulting urea base is recrystallized from acetic acid ethyl ester.

Yield: 18.5 g (77.9% of theoretical).
M.p.: 73° to 75° C.

The hydrochloride is obtained by dissolving the urea base with heating in acetone and adding dropwise with stirring at room temperature the equivalent amount of an ethereal solution of HCl.

M.p.: 153° to 157° C. (from acetic acid ethyl ester and little methanol).

EXAMPLE 5

N,N-Diethyl-N'-methyl-N'-3-morpholinopropyl-urea hydrochloride

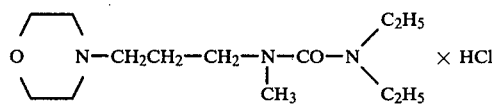

13 g (0.1 mole) of N,N-diethyl-N'methyl urea are dissolved in 100 cc. of anhydrous dioxane. 3.9 g (0.1 mole) of NaNH2 are added thereto and the reaction mixture is heated one hour at reflux. After cooling, 16.4 g (0.1 mole) of N-(3-chloropropyl)morpholine dissolved in 50 cc. of anhydrous dioxane are added thereto dropwise and the reaction mixture is refluxed for 6 hours. After cooling, the precipitated NaCl is filtered off with suction, the filtrate is evaporated and the remaining residue is subjected to fractionated distillation.

Yield: 12.5 g (48.6% of the theoretical)
B.p. 0.5 mm: 145° to 150° C.

For further purification, the crude base is dissolved in 50 cc. of methanol and is passed through a column of silicagel. A mixture of chloroform, methanol and benzene in a ratio of 2:1:1 is used as solvent. The thus purified base is dissolved in anhydrous ether and the equivalent amount of an ethereal solution of HCl is added thereto. The precipitated hydrochloride is filtered off and recrystallized from ethyl acetate.

M.p.: 130° to 132° C.

The compounds given hereinafter in Table 1 have been prepared by the processes described in the above examples using the appropriate starting materials.

TABLE 1

$$B-(CH_2)_p-N-\overset{O}{\underset{\|}{C}}-N-R_1 \times HCl$$
$$\phantom{B-(CH_2)_p-N}\underset{R_3}{|}\phantom{-C-}\underset{R_2}{|}$$

| Example | B | —(CH2)p— | R1 | R2 | R3 | M.p. °C. |
|---|---|---|---|---|---|---|
| 6 | | —CH2CH2— | C6H13 | CH3 | CH3 | 173–176 |
| 7 | | —CH2CH2— | C8H17 | CH3 | CH3 | 175–178 |
| 8 | 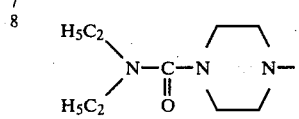 | —CH2CH2— | C10H21 | CH3 | CH3 | 170–173 |
| 9 | | —CH2CH2— | C12H25 | CH3 | CH3 | 171–173 |

TABLE 1-continued $$B-(CH_2)_p-\underset{R_3}{N}-\underset{\|}{\overset{O}{C}}-\underset{R_2}{N}-R_1 \times HCl$$

| Example | B | $-(CH_2)_p-$ | $R_1$ | $R_2$ | $R_3$ | M.p. °C. |
|---|---|---|---|---|---|---|
| 10 | | $-CH_2CH-$ | $C_{13}H_{27}$ | $CH_3$ | $CH_3$ | 167–169 |
| 11 | | $-CH_2CH_2-$ | $C_{14}H_{29}$ | $CH_3$ | $CH_3$ | 161–164 |
| 12 | | $-CH_2CH_2CH_2-$ | $C_{14}H_{29}$ | $CH_3$ | $CH_3$ | 118–120 |
| 13 | | $-CH_2CH_2-$ | $C_{14}H_{29}$ | $CH_3$ | $C_2H_5$ | 99–102 |
| 14 | | $-CH_2CH_2-$ | $C_{14}H_{29}$ | $C_2H_5$ | $C_2H_5$ | 78–84 |
| 15 | | $-CH_2CH_2-$ | $C_{14}H_{29}$ | $C_2H_5$ | $CH_3$ | 128–131 |
| 16 | | $-CH_2CH_2-$ | $C_{15}H_{31}$ | $CH_3$ | $CH_3$ | 167–169 |
| 17 | | $-CH_2CH_2-$ | $C_{16}H_{33}$ | $CH_3$ | $CH_3$ | 165–168 |
| 18 | | $-CH_2CH_2-$ | $C_{18}H_{37}$ | $CH_3$ | $CH_3$ | 163–166 |
| 19 | | $-CH_2CH_2-$ | $C_6H_{13}$ | $CH_3$ | $CH_3$ | 117–120 |
| 20 | | $-CH_2CH_2CH_2-$ | $C_8H_{17}$ | $CH_3$ | $CH_3$ | 95–97 |
| 21 | | $-CH_2CH_2-$ | $C_8H_{17}$ | $CH_3$ | $CH_3$ | 123–126 |
| 22 | | $-CH_2CH_2-$ | $C_{10}H_{21}$ | $CH_3$ | $CH_3$ | 128–135 |
| 23 | | $-CH_2CH_2CH_2-$ | $C_{10}H_{21}$ | $CH_3$ | $CH_3$ | 100–101 |
| 24 | O〈N-morpholino〉N— | $-CH_2CH_2-$ | $C_{12}H_{25}$ | $CH_3$ | $CH_3$ | 133–137 |
| 25 | | $-CH_2CH_2-$ | $C_{13}H_{27}$ | $CH_3$ | $CH_3$ | 134–138 |
| 26 | | $-CH_2CH_2-$ | $C_{14}H_{29}$ | $CH_3$ | $CH_3$ | 102 |
| 27 | | $-CH_2CH_2$ | $C_{14}H_{29}$ | $CH_3$ | $CH_3$ | 139–143 |
| 28 | | $-CH_2CH_2CH_2-$ | $C_{14}H_{29}$ | $CH_3$ | $CH_3$ | 105–106 |
| 29 | | $-CH_2CH_2CH_2-$ | $C_{14}H_{29}$ | $CH_3$ | $C_2H_5$ | 116–119 |
| 30 | | $-CH_2CH_2CH_2-$ | $C_{14}H_{29}$ | $C_2H_5$ | $C_2H_5$ | 109–113 |
| 31 | | $-CH_2CH_2-$ | $C_{15}H_{31}$ | $CH_3$ | $CH_3$ | 135–140 |
| 32 | | $-CH_2CH_2-$ | $C_8H_{17}$ | $CH_3$ | $CH_3$ | 158–161 |
| 33 | $H_3C-SO_2-N\langle\rangle N-$ | $-CH_2CH_2-$ | $C_{10}H_{21}$ | $CH_3$ | $CH_3$ | 159–162 |
| 34 | | $-CH_2CH_2-$ | $C_{14}H_{29}$ | $CH_3$ | $CH_3$ | 153–157 |
| 35 | | $-CH_2CH_2-$ | $C_{14}H_{29}$ | $CH_3$ | $CH_3$ | 159–162 |
| 36 | $H_3C-C_6H_4-CO-(CH_2)_2-N\langle\rangle N-$ | $-CH_2-CH_2-$ | $C_9H_{19}$ | $CH_3$ | $CH_3$ | 179–180[1] |
| 37 | | $-CH_2-CH_2-$ | $C_{12}H_{25}$ | $CH_3$ | $CH_3$ | 180–181[1] |
| 38 | | $-CH_2-CH_2-$ | $C_{14}H_{29}$ | $CH_3$ | $CH_3$ | 169–171[1] |
| 39 | $H_3C-O-C_6H_4-CO-(CH_2)_2-N\langle\rangle N-$ | $-CH_2CH_2-$ | $C_9H_{19}$ | $CH_3$ | $CH_3$ | 172–174[1] |
| 40 | $Cl-C_6H_4-CO-(CH_2)_2-N\langle\rangle N-$ | $-CH_2CH_2-$ | $C_{14}H_{29}$ | $CH_3$ | $CH_3$ | 177–179[1] |
| 41 | | $-CH_2CH_2-$ | $C_9H_{19}$ | $CH_3$ | $CH_3$ | 180–182[1] |
| 42 | $H_3C-C_6H_4-CO-CH_2-N\langle\rangle N-$ | $-CH_2CH_2-$ | $C_{12}H_{25}$ | $CH_3$ | $CH_3$ | 206–208[1] |
| 43 | | $-CH_2CH_2-$ | $C_{14}H_{29}$ | $CH_3$ | $CH_3$ | 202–204[1] |
| 44 | $H_3C-O-C_6H_4-CO-CH_2-N\langle\rangle N-$ | $-CH_2CH_2-$ | $C_{12}H_{25}$ | $CH_3$ | $CH_3$ | 199–201[1] |
| 45 | | $-CH_2CH_2-$ | $C_{14}H_{29}$ | $CH_3$ | $CH_3$ | 204–206[1] |
| 46 | $Br-C_6H_4-CO-CH_2-N\langle\rangle N-$ | $-CH_2CH_2$ | $C_9H_{19}$ | $CH_3$ | $CH_3$ | 197–198[1] |
| 47 | | $-CH_2CH_2-$ | $C_{12}H_{25}$ | $CH_3$ | $CH_3$ | 195–197[1] |
| 48 | | $-CH_2CH_2-$ | $C_{14}H_{29}$ | $CH_3$ | $CH_3$ | 212–213[1] |

[1] Fp. als Dihydrochlorid

Pharmaceutical preparation have been prepared from the compound of Example 19 as described in the following examples:

EXAMPLE 49

| Coated tablets, 50 mg. of urea base | |
| --- | --- |
| 1 tablet contains: | |
| N,N'-dimethyl-N-hexyl-N'-(2-morphilinoethyl)-urea hydrochloride | 56.4 mg. |
| Calciumhydrogenphosphate DAB 7 | 24.6 mg. |
| Talcum Eu.A.B. III | 5.0 mg. |
| Avicel PH 101 | 19.0 mg. |
| Corn starch Eu.A.B. I | 20.0 mg. |
| Aerosil 200 | 1.5 mg. |
| Polyplasdone XL | 7.5 mg. |
| Magnesium stearate USP XIX | 1.0 mg. |
| | 135.0 mg. |

N,N'-Dimethyl-N-hexyl-N'-(2-morpholinoethyl)-urea hydrochloride, calcium hydrogenphosphate and talcum are passed through a sieve having a mesh width of 1 mm, are mixed in a vortex granulator and are granulated by spraying with water. The relative humidity of the granulate should be 45%. Thereafter, the granulate together with Avicel, corn starch, Aerosil, Polyplasdone XL and magnesium stearate is passed through a sieve having a mesh width of 0.8 mm, and all components are mixed until a homogenous product is obtained. The resulting mixture is pressed to kernels having a diameter of 7 mm, a curvature radius of 5 mm and weighing each 135 mg.

The resulting kernels are film coated with 4 mg. each of a film consisting of lacquer, softening agent and color pigments in usual manners in a vortex coating machine.

EXAMPLE 50

| Injection solution, containing 0.1% of urea base per ml. | |
| --- | --- |
| Ampoules of 5 cc. (containing 5 mg. of active agent) | |
| Ampoules of 10 cc. (containing 10 mg. of active agent) | |
| 1 ml. contains: | |
| N,N'-dimethyl-N-hexyl-N'-(2-morpholinoethyl)-urea hydrochloride | 1.13 mg. |
| Sodium chloride | 4.30 mg. |
| Sodium dihydrogenphosphate DAB 7 | 1.97 mg. |
| Sodium monohydrogenphosphate DAB 7 | 19.30 mg. |
| Water for injection filled up to | 1.0 ml. |

The active agent and the other components are dissolved in part of the water for injection and the solution is filled up to the final volume.

The solution is subjected to sterile filtration through a membrane filter under nitrogen and is filled into the ampoules under aseptic conditions to give (a) clear glass ampoules containing 5.3 ml. of the solution and (b) clear glass ampoules containing 10.5 ml. of the solution.

EXAMPLE 51

| Skin gel containing 0.03% of urea base | |
| --- | --- |
| 1 g of gel contains: | |
| N,N'-dimethyl-N-hexyl-N'-(2-morpholinoethyl)-urea hydrochloride | 0.34 mg. |

| -continued | |
| --- | --- |
| Skin gel containing 0.03% of urea base | |
| Sodium dihydrogenphosphate DAB 7 | 10.25 mg. |
| Sodium monohydrogenphosphate DAB 7 | 0.36 mg. |
| Phenethanol DAC | 5.00 mg. |
| Natrosol 250 HHR | 18.00 mg. |
| Purified water Eu.A.B. I, filled up to | 1000.00 mg. |

The active agent, the phosphates and Phenethanol are dissolved in water whereafter the Natrosol is admixed in a high speed dispersion machine. The mixture is heated to 40° C. with stirring resulting into a clear homogenous gel.

EXAMPLE 52

| Creme o/w containing 0.03% of the urea base | |
| --- | --- |
| 1 g of the creme contains: | |
| N,N'-dimethyl-N-hexyl-N'-(2-morpholinoethyl)-urea hydrochloride | 0.34 mg. |
| Arlatone 983 (Atlas) | 60.00 mg. |
| Cetostearyl alcohol DAB 7 | 20.00 mg. |
| Stearic acid | 40.00 mg. |
| Paraffin. perliqu. DAB 7 | 100.00 mg. |
| Oleum neutrale DAC | 55.00 mg. |
| Phenethanol DAC | 10.00 mg. |
| Glycerin DAB 7 | 30.00 mg. |
| Purified water EU.A.B. I, filled up to | 1000.00 mg. |

The Arlatone, Cetostearyl alcohol, stearic acid, paraffine, neutral oil and half of the Phenethanol are molten with heating to 60° C. in a container with a suitable stirrer of a high speed disperging machine. The active agent, glycerine and the remaining amount of Phenethanol are dissolved in the necessary amount of water and are also heated to 60° C. The aqueous phase is admixed homogenously into the fatty phase by means of the dispersing machine and the mixture is cooled to 30° C. with running stirrer.

EXAMPLE 53

| Eye ointment, 0.03% of urea base | |
| --- | --- |
| 1 g of the ointment contains: | |
| N,N'-dimethyl-N-hexyl-N'-(2-morpholinoethyl)-urea | 0.3 mg. |
| Benzyl alcohol | 5.0 mg. |
| Eucerin, anhydricum | 200.0 mg. |
| High viscosity paraffine | 299.7 mg. |
| White vaseline | 500.0 mg. |

Eucerin, anhyricum, paraffine and vaseline are molten and mixed and sterilized for 3 hours at 140° C. Thereafter, the active agent and the benzyl alcohol are dissolved under aseptic conditions in the still liquid base and the mixture thereafter is cooled.

EXAMPLE 54

| Eye drops, 0.03% of urea base | |
| --- | --- |
| 1 cc. of the eye drops contains: | |
| N,N'-dimethyl-N-hexyl-N'-(2-morpholinoethyl)-urea | 0.34 mg. |
| Polyvinyl alcohol | 10.00 mg. |
| Phenethanol DAC | 5.00 mg. |
| Sodium chloride p.a. | 7.10 mg. |
| Injection water, filled up to | 1.00 cc. |

What we claim is:

1. Basically substituted ureas of the general Formula I

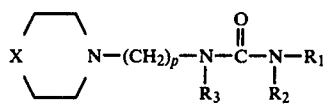

wherein

X is the group $R_4$—N<, p is 2 or 3, $R_1$ is an alkyl group having from 6 to 18 carbon atoms, $R_2$ and $R_3$, which may be the same or different from each other, are methyl or ethyl and $R_4$ is the methyl sulfonyl group, the diethyl carbamoyl group or the group

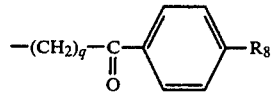

wherein q is 1 or 2 and $R_8$ is methyl, methoxy, chlorine or bromine, and the pharmacologically acceptable salts thereof.

2. N,N'-Dimethyl-N-n-tetradecyl-N'-[2-(1-diethyl-carbamoyl-4-piperazinyl)-ethyl]-urea and its pharmaceutically acceptable acid addition salts.

3. N,N'-Dimethyl-N-n-tetradecyl-N'-{2-[1-(2-p-toluyl-ethyl]-4-piperazinyl]-ethyl}-urea and its pharmaceutically acceptable acid addition salts.

4. Process for the treatment of humans or animals suffering from a diseases caused by viruses comprising administering to said human or animal a compound according to claim 1 topically in a dose ranging from 0.005 to 0.3 percent by weight or parenterally in a daily dose ranging from 5 to 250 mg per kg body weight of the human or animal to be treated.

5. Process according to claim 4 wherein the active compound according to claim 1 is administered topically in a dose ranging from 0.01 to 0.1 percent by weight and parenterally in a daily dose ranging from 10 to 200 mg per kg.